United States Patent [19]

Hofmann

[11] Patent Number: 5,077,038

[45] Date of Patent: Dec. 31, 1991

[54] NAIL POLISH REMOVER

[75] Inventor: William H. Hofmann, St. Louis, Mo.

[73] Assignee: Vi-Jon Laboratories, Inc., St. Louis, Mo.

[21] Appl. No.: 555,786

[22] Filed: Jul. 19, 1990

Related U.S. Application Data

[63] Continuation of Ser. No. 386,304, Jul. 27, 1989, abandoned.

[51] Int. Cl.$^5$ ............................................. A61K 7/047
[52] U.S. Cl. .................................... 424/61; 252/364; 252/546; 134/38
[58] Field of Search .......................... 424/61; 134/38; 252/364, 546

[56] References Cited

U.S. PATENT DOCUMENTS

| | | | |
|---|---|---|---|
| 4,485,037 | 11/1984 | Curtis | 424/61 |
| 4,735,798 | 4/1988 | Bernstein | 424/61 |
| 4,824,662 | 4/1989 | Hofmann | 424/61 |

*Primary Examiner*—Thurman K. Page
*Assistant Examiner*—James M. Spear
*Attorney, Agent, or Firm*—Armstrong, Teasdale, Schlafly & Davis

[57] ABSTRACT

A nail polish remover base comprising less than 79% acetone or less than 81% ethyl acetate combined with water or a mixture of a water and ethanol to produce a 100% by weight of the base. The base can be combined with vegetable or animal protein, perfumes, surfactants and coloring agents to produce a final nail polish remover.

2 Claims, No Drawings

NAIL POLISH REMOVER

This is a continuation of application Ser. No. 386,304, filed on July 27, 1989, now abandoned.

BACKGROUND OF THE INVENTION

The present invention relates to a novel composition for removing nail lacquer and in particular the present invention relates to a novel base utilizing more water and less solvent than is conventionally used in leading nail polish remover compositions.

Many compositions are known which are useful in removing lacquer from fingernails or toenails. These compositions depend primarily upon the solvent action of acetone or an acetone-like solvent to soften or dissolve the nail lacquer. After the lacquer has been dissolved or softened, it is usually removed by a gentle abrasive or by a gentle rubbing action.

In addition to acetone, ethyl acetate is a well known solvent used in nail polish removers.

These solvents readily remove the nail lacquer. However, when used alone they have a dehydrating effect on the nails of the user, rendering the nail dry, hard and susceptible to cracking and breaking.

Usually the solvents used in commercial nail polish removers all contain other materials, such as water and/or various oils, which not only lower the dehydrating effect of the solvents, but also are believed to lower the enamel dissolving efficiency of the solvents.

I unexpectedly discovered that uses of enamel removal solvents of the ethyl acetate and acetone types in amounts substantially below those amounts formally considered efficacious result in superior bases for lacquer removers. Specifically, I have found that amounts of ethyl acetate in the range of 60–81% combined with 19–35% water and alcohol combinations result in a superior nail polish remover base which does not have drying effects on the skin or cause whitening of the nails. I also have found that with acetone based lacquer removers, a superior polish remover base is formed when 60–84% acetone is combined with 21–35% water to form a nail polish remover base. Preferably my new base contains less than about 70% acetone or ethyl acetate and up to about 30% water, ethanol, isopropanol or mixtures thereof.

Accordingly, a principal object of this invention is to provide novel nail polish remover bases which utilize substantially more water and less solvent and to minimize the dehydration of skin and nails to which they are applied. Another object of this invention is to provide a nail polish remover base which has economic advantages and which result in an efficacious product without skin drying or nail whitening properties.

U.S. Pat. No. 4,824,662 of which I am the inventor and which is assigned to the assignee of this application describes a lacquer remover having a hydrolyzed soy protein in combination with 82–88% ethyl acetate or 85–90% acetone and a surfactant.

I also am aware of U.S. Pat. No. 4,485,037 which claims to lower water removal activity of acetone base nail polish removers by adding collagen in combination with an acid addition salt of amidized trialkylamine cationic surfactant.

U.S. Pat. No. 4,032,464 describes a creamy nail lacquer remover containing a chelating agent, a suitable humectant, such as propylene glycol, 2-hydroxy-4-methoxy-benzophenone-5-sulfonic acid, a collagen-derived protein-fatty acid condensation product and a carboxy vinyl polymer. This material too has an acetone base.

U.S. Pat. No. 2,765,257 shows a combination of solvent and sulfonated mineral oil in which the solvent includes acetone, butyl acetate, dibutyl phthalate and butyl acetyl ricinoleate.

This invention involves a base for nail polish removers which contains less than 79% acetone or less than 81% ethyl acetate as a main solvent and the remainder of the solvent base comprises water or a mixture of water and ethanol or isopropanol in the case of ethyl acetate. To this base are conventionally added conditioners which may be a water soluable amine salt of a fatty acid amide of a hydrolyzed soy protein or an amidized hydrolyzed collagen derivative which renders the hydrolyzed collagen anionic, a surfactant, and suitable perfumes and coloring agents, viscosity raising agents, emolients, etc.

Conventionally a film forming material, such as nitrocellulose, is incorporated into nail polish removers to inhibit moisture loss from the nails. It is another object of this invention to obviate the necessity for using such added expensive ingredients.

These and other objects and advantages will become apparent hereinafter.

SUMMARY OF THE INVENTION

This invention relates to nail polish remover base formulation in which reduced amounts of lacquer solvent are mixed with increased amounts of water and/or ethyl alcohol or isopropanol to produce a base to which other ingredients can be added and in which the final composition has substantially reduced skin and nail moisture removal characteristics.

The invention also consists in the parts and the arrangements and combinations of parts and ingredients hereinafter described and claimed.

DETAILED DESCRIPTION

In all of the examples and discussion which follow, all percentage figures are percent-by-weight of the finished formulation.

The nail enamel removers of this invention are primarily of two types, as follows:

1. Ethyl Acetate Base
   Ethyl Acetate 65–81%
   Ethanol, isopropanol, water 19–35%
   The evaporated total solids of all conditioners is about 2.5/3.5%

2. Acetone Base
   Acetone 65–79%
   Water 35–21%
   Conditioners 0.20/0.50%
   The evaporated total solids of all conditioners is about 0.15/0.25%

The foregoing bases are combined with a mixture of a surfactant and aminomethylpropanol salt of isostearic amide of hydrolyzed soy isolate protein in the amounts and of the types described in U.S. Pat. No. 4,824,662 which is herein incorporated by reference. Preferably about 0.05 to about 0.25% soy protein salt is added to the solvent, and about 0.1 to about 0.3% surfactant are used.

In addition, the foregoing bases can be combined with an amidized hydrolyzed collagen derivative which renders the hydrolyzed collagen anionic, preferably in the amount of 0.01% to about 0.15% as shown and described in U.S. Pat. No. 4,485,037 which is hereby incorporated herein by reference.

In addition to the aforementioned ingredients, 0.2 to about 0.3% of a desired perfume or fragrance can be added to the composition and about 0.1-0.3% of a suitable coloring material can be incorporated into the composition.

Following are specific examples of the invention.

EXAMPLE 1

| Composition | | Characteristics |
|---|---|---|
| Acetone | 70.0% | Color - Optional |
| Water | 29.3% | Opacity/Clarity |
| Hydrolyzed Soy Protein | 0.25% | Polish Removal - Good |
| Surfactant | 0.25% | Whitening of Nails - None |
| Perfume | 0.20% | Drying of Skin - None |
| Sp. Gravity | 0.8786% | |

EXAMPLE 2

| Composition | | Characteristics |
|---|---|---|
| Ethyl Acetate | 60.0% | Color - Optional |
| Water | 10.0% | Opacity/Clarity |
| Ethanol/Isopropanol | 26.0% | Polish Removal - Good |
| Hydrolyzed Soy Protein | 0.05% | Whitening of Nails - None |
| Surfactant | 0.25% | Drying of Skin - None |
| Perfume | 0.40% | |
| Sp. Gravity | 0.895% | |

It is clear from the foregoing Examples that the use of acetone and ethyl acetate solvents in a nail polish remover base at levels substantially below those previously thought necessary results in an efficacious product which also has no drying of the skin or whitening of the nails of the user.

In addition to the nail enamel remove bases, the final nail remove composition comprises a mixture composed of a surfactant, cocamidopropyl dimethylamine propionate used at the 0.10% to 0.30% level and aminomethylpropanol salt of isosteric hydrolyzed soy protein used at the 0.05% to 0.25% level depending on the type of solvent base employed.

The hydrolyzed soy proteins hereinbefore described are only water soluble and compatible with up to 50% aqueous alcohol. They are not compatible with conventional mail polish removers without further treatment.

To achieve compatibility with aqueous acetone, a further processing step, amidization of the protein is required. This can be substantially represented by the following formula:

where:

R' = Fatty Acid of 5-22 carbons (preferably isostearic acid—18 carbons)

R = Side-chain groups characteristic of amino acids in soya protein n = Integer from 10 to 40

The conversion of accessible primary amine groups of hydrolyzed soya protein (including the sidechain or epsilon amino groups, such as Arginine and Lysine—a key essential amino acid) to amide groups, imparts an anionic charge to the hydrolyzed soy protein. This enables it to form stable salts with bases: organic amines, such as alkyl and hyroxyalkyl amines of 1-4 carbon atoms, e.g., trimethylamine, diethylamine, etc; and alkanolamines of 1-4 carbon atoms, such as, ethanolamine, propanolamine, aminomethylpropanol, etc. The exact nature of the amine which forms the salt is not critical, as long as the salt formed is cosmetically acceptable and is soluble in aqueous acetone.

The preferred product is a salt of a fatty acid amide of hydrolyzed soy protein, i.e., the aminomethylpropanol salt of isotearic amide of hydrolyzed soya isolate protein. This product is available from Brooks Industries Inc., 70 Tyler Place, South Plainfield, N.J. 07080, under the trademark of "Etha-Soy Iso" as a light yellow clear liquid with a solids content of 27-35% (after drying for 16 hours at 105° C.), a pH 7.0-9.5 (10% aqueous solution at 25° C.), a specific gravity of 0.830-0.880 (at 25% C.), and an acid value of 35.0-50.0.

The hydrolyzed soya protein has an average molecular weight of 1000 to 4000.

This invention is intended to cover all changes and modifications of the examples of the invention herein chosen for purposes of the disclosure which do not constitute departures from the spirit and scope of the invention.

What is claimed is:

1. A nail polish remover having low total solvent concentrations consisting essentially of a polish remover base having an active ingredient selected from the group consisting of acetone and ethyl acetate in which acetone is present in an amount between 60% and less than 79% by weight and water is present form 21 to 40% by weight or ethyl acetate is present in an amount between about 60% to less than 81% by weight and water is present in an amount between 19-35% by weight; and the remainder of the base is selected from the group consisting of ethanol, isopropanol, nd mixtures thereof; the nail polish remover having from about 0.05 to about 0.25% by weight of a cosmetically acceptable salt of a hydrolyzed soy protein having a molecular weight of between about 1000-4000, and from about 0.1 to 0.3% by weight of a cocamidopropyl dimethylamine propionate, the combination being effective to substantially completely remove nail polish without drying of the nail and surrounding skin.

2. The nail polish remover of claim 1 wherein the base contains less than about 70% acetone and up to about 30% water, ethanol, isopropanol or mixtures thereof.